(12) United States Patent
Debatty et al.

(10) Patent No.: US 10,124,191 B2
(45) Date of Patent: Nov. 13, 2018

(54) HADRON THERAPY INSTALLATION COMPRISING AN IMAGING DEVICE

(71) Applicant: ION BEAM APPLICATIONS S.A., Louvain-la-Neuve (BE)

(72) Inventors: Alexandre Debatty, Hevillers (BE); Jean-Claude Amélia, Erquelinnes (BE); Sébastien De Neuter, Jandrenouille (BE)

(73) Assignee: Ion Beam Applications S.A., Louvain-la-Neuve (BE)

( * ) Notice: Subject to any disclaimer, the term of this patent is extended or adjusted under 35 U.S.C. 154(b) by 816 days.

(21) Appl. No.: 14/426,913

(22) PCT Filed: Sep. 10, 2013

(86) PCT No.: PCT/EP2013/068763
§ 371 (c)(1),
(2) Date: Mar. 9, 2015

(87) PCT Pub. No.: WO2014/041004
PCT Pub. Date: Mar. 20, 2014

(65) Prior Publication Data
US 2015/0246245 A1    Sep. 3, 2015

Related U.S. Application Data

(60) Provisional application No. 61/700,700, filed on Sep. 13, 2012.

(30) Foreign Application Priority Data

Sep. 11, 2012  (BE) .................................. 2012/0604

(51) Int. Cl.
*A61N 5/10*     (2006.01)
*A61B 6/03*     (2006.01)
(Continued)

(52) U.S. Cl.
CPC ............ *A61N 5/1048* (2013.01); *A61B 6/032* (2013.01); *A61B 6/035* (2013.01); *A61B 6/4085* (2013.01);
(Continued)

(58) Field of Classification Search
CPC .. A61N 5/1048; A61N 5/1081; A61N 5/1049; A61N 2005/1061;
(Continued)

(56) References Cited

U.S. PATENT DOCUMENTS

| 2003/0007601 | A1 | 1/2003 | Jaffray et al. |
| 2009/0065717 | A1* | 3/2009 | Kaiser ................. A61N 5/1049 250/505.1 |
| 2009/0304153 | A1* | 12/2009 | Amelia ................ A61N 5/1049 378/65 |

FOREIGN PATENT DOCUMENTS

| EP | 2 047 888 | 4/2009 |
| EP | 2 377 576 | 10/2011 |
| WO | WO 2006/060886 | 6/2006 |

OTHER PUBLICATIONS

International Search Report dated Feb. 25, 2014 for International Application No. PCT/EP2013/068763 filed Sep. 10, 2013. (11 pgs).

* cited by examiner

*Primary Examiner* — Peter Luong
(74) *Attorney, Agent, or Firm* — Finnegan, Henderson, Farabow, Garrett & Dunner LLP

(57) ABSTRACT

The invention relates to a hadron therapy installation that comprises an irradiation unit (1) supported by a rotary support structure, so as to be able to rotate around a target volume (15) centered on the axis of rotation (22), to deliver a treatment beam (17) from different angles on the target volume (15). An imaging device (3, 4) is secured in rotation with the irradiation unit (1) and translatable relative to the irradiation unit (1) between a retracted position at the irradiation unit (1) and a lateral deployed position relative to the target volume (15), such that in its deployed position, the imaging device (3, 4) can rotate around the target volume (15) together with the irradiation unit (1). Such an installation can be used for a cone beam computed tomography method and/or a fluoroscopic imaging method on a patient to be treated in the hadron therapy installation.

17 Claims, 8 Drawing Sheets

(51) Int. Cl.
*A61B 6/00* (2006.01)
*A61B 6/10* (2006.01)
(52) U.S. Cl.
CPC ............ *A61B 6/487* (2013.01); *A61N 5/1049* (2013.01); *A61N 5/1081* (2013.01); *A61B 6/105* (2013.01); *A61B 6/4429* (2013.01); *A61B 6/547* (2013.01); *A61N 2005/1061* (2013.01); *A61N 2005/1087* (2013.01)
(58) Field of Classification Search
CPC ............ A61N 2005/1087; A61B 6/035; A61B 6/487; A61B 6/4085; A61B 6/032; A61B 6/4429; A61B 6/105; A61B 6/547
See application file for complete search history.

HADRON THERAPY INSTALLATION COMPRISING AN IMAGING DEVICE

TECHNICAL FIELD

The present invention relates to a hadron therapy installation comprising an imaging device. It also relates to an imaging method using cone beam computed tomography, as well as a fluoroscopy method in such a hadron therapy installation.

BACKGROUND OF THE INVENTION

The recent hadron therapy techniques for treating cancer make it possible to deliver a dose precisely on a target volume, for example a tumor, while preserving the surrounding tissue. Such a hadron therapy installation comprises a particle accelerator producing a charged particle beam, means for transporting the beam, and an irradiating unit. The irradiating unit delivers a dose distribution on the target volume and generally comprises means for monitoring the delivered dose, for example such as an ionizing chamber, as well as monitoring means for the beam, for example such as a collimator or scanning magnets based on the delivery mode of the beam used.

Most hadron therapy installations comprise a rotary gantry supporting a system for delivering the beam comprising a beam transport line ending with an irradiation unit, which my als be called a beam outlet unit. The rotary gantry is capable of rotating 360° around a horizontal axis of rotation, such that the irradiation unit can deliver a treatment beam from several irradiation angles. In the more compact recent hadron therapy installations, the irradiation unit may only rotate by an angle smaller than 360° around a horizontal axis of rotation.

Often, hadron therapy treatment occurs over several sessions. The patient must be positioned correctly before each treatment session. The position of the target volume to be treated is generally determined relative to a reference point situated in the patient's body. This determination is made using an imaging device, for example such as a PET scan. The patient is then positioned so that the target line to be treated coincides with a point of the treatment space called the isocenter. The isocenter is defined as a point in space at the intersection between the horizontal axis of rotation of the gantry and the central axis of the beam delivered by the irradiation unit at multiple incline angles of the gantry. In practice, all of the central beam axes delivered at several incline angles of the gantry do not intersect at a single point, but each intercept a small spherical or ellipsoid volume. The center of mass of said spherical or ellipsoid volume is generally defined as the isocenter of the rotary gantry. This isocenter is for example determined using the method described in document U.S. Pat. No. 7,349,523 or the method described in document EP2186542.

The patient must be positioned precisely relative to said isocenter. The patient is first pre-positioned using positioning means capable of locating reference point situated in or on the patient's body. For example, references are marked on the patient's skin so as to coincide with those of the laser beam. A second means may be an x-ray source and a detection panel positioned in a stationary manner on either side of the patient in the treatment area, so as to view references comprised in the bone structure of the patient or markers pre-inserted into the target volume to be treated and visible by x-ray imaging.

In order to allow more precise positioning of the patient, an imaging device using cone beam computed tomography, commonly called CBCT, is used. Such a device comprises equipment for producing x-rays and equipment for receiving x-rays, which can be positioned on either side of the patient and pivoted around the patient, so as to take a plurality of images designed to be processed by a computer to reconstruct a three-dimensional image of the inside of the patient's body. The obtained three-dimensional image makes it possible to view both the bone structure and the soft tissues. The therapist may also adjust the position of the patient more finely.

Document EP2243515 describes a hadron therapy installation comprising an x-ray device for emitting x-rays toward the target volume. This x-ray producing equipment is integrated into a nozzle providing the target volume with the beam of charged particles. It can pivot, inside said nozzle, between a first position, in which is arranged in the trajectory of the charged particle beam, and a second position, in which it is arranged outside the trajectory of the charged particle beam. X-ray receiving equipment is mounted across from the nozzle relative to the patient, and forms an optical alignment with the x-ray source when the x-ray producing equipment is in the first position.

Other installations comprising a similar imaging device are described in document EP1454653 and WO9818523. These three imaging devices are provided to perform "beam eye view" simulations, so as to verify that the orientation of the target volume to be treated coincides with the field of the treatment beam. In these imaging devices, the x-ray receiving equipment must be able to rotate synchronized with the x-ray producing equipment, so as to be able to form the optical alignment with the x-ray source. A device allowing the movement of the x-ray receiving equipment synchronously with the x-ray producing equipment must advantageously be relatively compact, so as to facilitate access to the patient. Such a device must not collide with the enclosure surrounding the treatment area, or with the support arms of the patient's bad.

Other imaging devices intended for the positioning of the patient in a hadron therapy installation are described in document US20080219407 and US20090065717. These imaging devices comprise x-ray producing equipment and x-ray receiving equipment mounted on a rotary arm in the shape of an arc of circle. These imaging devices have the drawback of cluttering the treatment area. Furthermore, collisions between the arms supporting the x-ray producing and receiving devices and the irradiation unit may occur.

Another imaging device is described in document WO2006060886 and comprises a rotary structure fastened on a vertical wall forming the bottom of the treatment area. The rotary structure is provided with:

a first telescoping or folding arm, which in turn is provided with x-ray producing equipment; and a second telescoping or folding arm, which in turn is provided with x-ray receiving equipment.

The rotary structure is configured to pivot around the patient with the arms extended or unfolded depending on the embodiment of the arms, while the rotary gantry of the hadron therapy installation is immobilized. This device requires means for monitoring the rotation of the rotary structure to avoid collisions with the irradiation unit. Although the bulk is reduced relative to CBCT devices mounted on rotary arms in the shape of an arc of circle, it would be advantageous to reduce this bulk even more and facilitate access to the patient, in particular when the arms are extended or unfolded.

Document WO2010076270 describes a hadron therapy installation comprising a rotary gantry supporting a beam transport line ending with an irradiation unit capable of delivering a treatment beam. The installation also comprises a moving floor that can be driven by the rotation of the gantry. According to one embodiment as described in this document, the installation comprises a cone beam computed tomography device comprising an x-ray source and x-ray receiving equipment. The x-ray source is positioned on a telescoping arm connected to the rotary gantry, so as to deliver a conical beam whereof the central axis is orthogonal to the central axis of the treatment beam. The x-ray receiving equipment can either be attached on an arm connected to a vertical wall forming the bottom of the treatment area and capable of rotating with the gantry, or on a rotary structure positioned outside the treatment area. The position of the x-ray source requires the presence of an opening in the moving floor to allow the x-ray beam to pass through the moving floor. Furthermore, the rotation of the x-ray receiving equipment must be perfectly synchronized with the rotation of the gantry, so as to preserve the alignment of the x-ray source with the isocenter and the x-ray receiving equipment.

It is desirable to position an integrated imaging device in a hadron therapy installation. This imaging device must advantageously be relatively compact, more particularly during installation and positioning of the patient by the therapist. Such an imaging device should be able to be used to carry out a cone beam computed tomography and fluoroscopy method. It is also desirable for the imaging device to be able to be integrated into a hadron therapy installation, for example comprising a moving floor whereof one portion is planar and aligned with the floor of the treatment room, as described in applications WO2010076270 or in the Belgian or US patent application filed that same day by the applicant, both incorporated by reference.

BRIEF DESCRIPTION OF THE INVENTION

A hadron therapy installation according to the present invention comprises a support structure capable of rotating about an axis of rotation, and an irradiation (or beam outlet) unit supported by that support structure, so as to be able to rotate around a target volume centered on the axis of rotation, to deliver a treatment beam from different angles on the target volume. It furthermore comprises an imaging device movable in rotation with the irradiation unit and translatable relative to the irradiation unit between a retracted position laterally of the irradiation unit and a deployed position laterally of the target volume, such that in its deployed position, the imaging device can rotate around the target volume together with the irradiation unit.

The imaging device preferably comprises a first driving means for a first piece of equipment of the imaging device. This first driving means preferably comprises: a first arm supporting the first piece of equipment; a cradle supporting the first arm, wherein the first arm is connected to the cradle by means of an articulation, preferably a cylindrical articulation; and a guide device arranganged alongside the irradiation unit and movable in rotation with the latter, so as to be able to guide the cradle in translation along the irradiation unit, in a direction essentially parallel to the direction of the treatment beam, to move the first piece of equipment from the retracted position, in which it is located laterally of the irradiation unit, into the deployed position, in which it is located laterally of the target volume; and a pivoting device to pivot the first arm about the cylindrical articulation, so as to cause the first piece of equipment to move laterally away from the target volume, when the first piece of equipment tends toward the deployed position.

It will be noted that such an arrangement of the imaging device in the hadron therapy installation requires a very reduced bulk. In its position retracted at the irradiation unit, the imaging device hinders the access to the patient as little as possible. In its lateral deployed position relative to the target volume, the imaging device is ideally arranged to take images during the treatment of the patient and to have an optimal view of the target volume. The fact that the imaging device is secured in rotation with the irradiation device prevents any risk of collision with the latter. The translational movement relative to the irradiation unit between the retracted position and the deployed position is a movement that takes up little space and also reduces the risk of accidental collisions. This translational movement may furthermore be implemented with relatively simple and very reliable means. It will further be appreciated that the combination of a translation and a pivoting movement of the first arm makes it possible to obtain an optimal arrangement of the imaging device deployed relative to the target volume, while ensuring a compact retracted position thereof.

Such an imaging device advantageously comprises x-ray producing equipment and x-ray receiving equipment, which, in the deployed position of the imaging device, are arranged on either side of the target volume.

Most often, the imaging device will further comprise a second arm, bearing a second piece of equipment of the imaging device, for example x-ray receiving equipment. A single cradle may then support the first arm and the second arm. If one wishes to have the possibility of moving the two pieces of equipment independently, it is preferable to have a second cradle supporting the second arm, and a second guide device arranganged alongside the irradiation unit and movable in rotation with the latter, so as to be able to guide the second cradle along the second irradiation unit to move the second piece of equipment from its retracted position to its to deployed position. In both solutions, the first arm and the second arm are advantageously arranged on either side of a plane containing the axis of rotation and the axis of the treatment beam.

Different mechanisms may be used to drive such a cradle in its guide device, for example such as a belt or endless chain, a hydraulic or pneumatic piston, a linear motor, etc.

In a preferred embodiment, the device for driving the cradle comprises a pinion supported by the cradle and rotated by a motor, and a rack that is stationary relative to the irradiation unit and arranged such that the pinion meshes in the rack to move the cradle in its guide device along the irradiation unit.

Different mechanisms may be used to generate this pivoting of the first arm about the cylindrical articulation, for example such as a motor with a gear transmission, a hydraulic or pneumatic piston, a cam mechanism, etc.

One simple and reliable embodiment of the device for pivoting the first arm comprises a guideway, which is immobile in a reference system secured to the irradiation unit, and a slide, which is supported by the first arm and arranged slidingly in the guideway. This guideway then comprises a first linear guide portion, to impart a translational movement to the first arm starting from its retracted position, such that the first arm remains substantially parallel to itself during said first translational movement, and a second curved guide portion, to give the first arm a pivoting movement about cylindrical articulation, that pivoting movement being superimposed on the translational movement so as to cause the first piece of imaging equipment to move laterally away from the target volume, when the first piece of equipment comes closer to the target volume.

In one preferred embodiment, in which the imaging device comprises a first arm, on which a first piece of imaging equipment is fastened, and/or a second arm, on which a second piece of imaging equipment is fastened, the irradiation unit advantageously comprises a cover forming an outer casing of the irradiation unit, and the cover comprises, on the side facing the target volume, a first opening for the passage of the treatment beam, a second opening for the passage of the first arm, and/or a third opening for the passage of the second arm.

In this advantageous embodiment, the first piece of equipment and/or the second piece of equipment of the imaging device are, in their respective retracted positions, completely or practically completely received inside the cover. Thus, any risk of collision of an object or person with the imaging device in the retracted position is avoided as effectively as possible.

One preferred embodiment of this imaging device comprises a piece of x-ray producing equipment and a piece of x-ray receiving equipment. The x-ray producing equipment comprises an x-ray source and a collimator. This collimator is situated between the source and the x-ray receiving equipment. The x-ray receiving equipment comprises an x-ray detection panel.

A cone beam computed tomography imaging method that uses a hadron therapy installation according to the invention, in which the imaging device comprises x-ray producing equipment and x-ray receiving equipment, comprises the following steps:

i) positioning the patient in the treatment area in the hadron therapy installation;
ii) deploying the x-ray producing equipment and the x-ray receiving equipment from the retracted position toward the deployed position, in which the x-ray producing equipment and the x-ray receiving equipment are arranged on either side of the target volume of the patient; and
iii) acquiring radiographic images during pivoting of the irradiation unit around the target volume.

In one preferred embodiment of this method, the following steps are carried out:
a) the field of view of the zone to be imaged is first defined;
b) the cone angle of the XR beam as well as the surface area necessary for the detection of the XR beam cone are calculated, based on the source-detector distance SID and source-treatment beam axis distance SAD;
c) the size of the field of view FOV to be imaged is compared to the ratio of the length of the detection panel to the enlargement factor L/MR; and
d) when the field of view FOV is smaller than or equal to the ratio of the length of the detection panel to the enlargement factor L/MR:
   steps i) to iii) are carried out; and
   a fourth step is carried out for computer processing of the obtained images to obtain a three-dimensional reconstruction of the inside of the patient's body; and
e) when the field of view FOV is greater than the ratio of the length of the detection panel to the enlargement factor L/MR:
   the patient is positioned according to step i);
   step ii) is carried out, by positioning the detection panel so as to capture a first portion of the x-ray beam cone, and by positioning the collimators so as to cover only the surface of the detection panel;
   step iii) is carried out;
   step i) is then carried out again, by repositioning the detection panel so as to pick up a second portion of the x-ray beam cone overlapping the first portion, and by positioning the collimators so as to cover only the surface of the detection panel; and
   step iii) is then carried out again;
   a fourth step is carried out for computer processing of the obtained images to obtain a three-dimensional reconstruction of the inside of the patient's body.

A fluoroscopy imaging method that uses a hadron therapy installation according to the invention, in which the imaging device comprises x-ray producing equipment and x-ray receiving equipment, comprises the following steps:
a) positioning a patient in a treatment area of the hadron therapy installation;
b) deploying the x-ray producing equipment and x-ray receiving equipment from the retracted position toward their deployed position; and
c) viewing the movement of the patient's organs using the x-ray producing equipment and the x-ray receiving equipment, the rotation of the irradiation unit being immobilized.

BRIEF DESCRIPTION OF THE DRAWINGS

To better understand the invention and its advantages, one preferred embodiment and several alternative embodiments thereof are described as an illustration and non-limitingly, in reference to the appended drawings, in which:

FIG. 4a: is a three-dimensional view of an irradiation unit with an imaging device shown in a deployed position;

FIG. 4b: is a front view of the irradiation unit as shown in FIG. 4a;

FIG. 5a: is a three-dimensional view of an irradiation unit with an imaging device shown in a retracted position;

FIG. 5b: is a frontal view of the irradiation unit as shown in FIG. 5a;

DETAILED DESCRIPTION OF THE INVENTION

Figure 1:
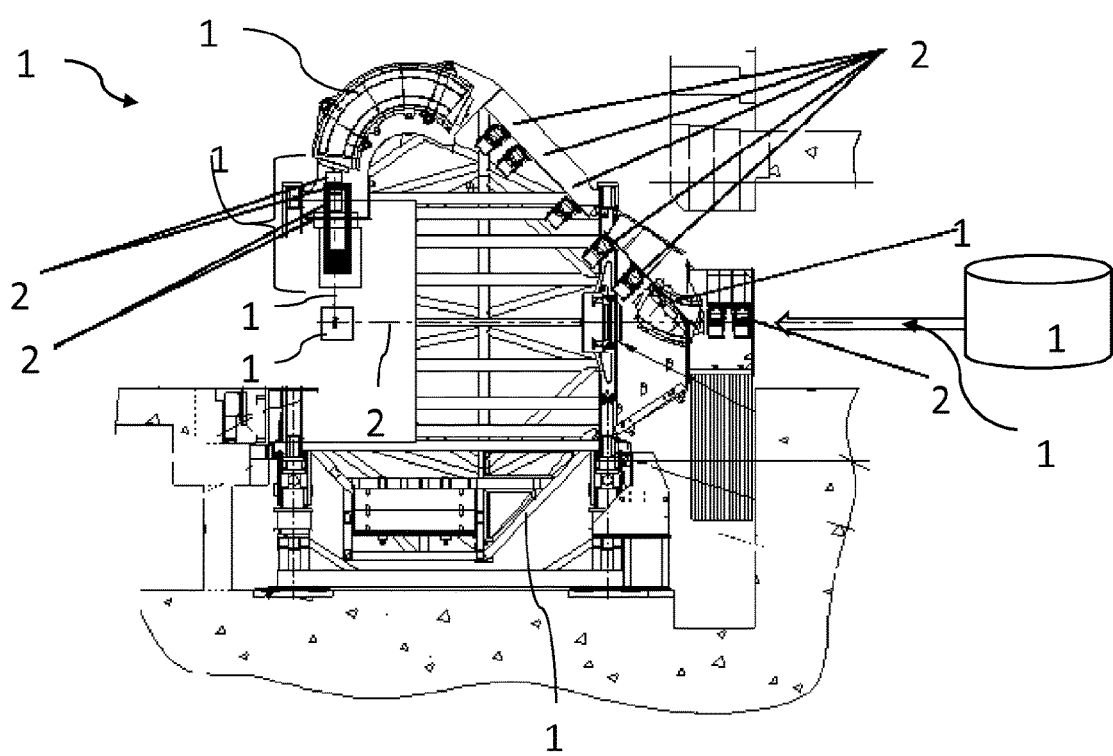
FIG. 1: is a very diagrammatic vertical cross-section of a hadron therapy installation according to a first embodiment.

FIG. 1 shows a first embodiment of the hadron therapy installation 100. This installation comprises: a generator 16 capable of generating a hadron beam 17, for example a cyclotron, a synchrotron or a synchrocyclotron; an isocentric rotary gantry 18 capable of rotating by an angle of 360° about the axis of rotation 22; and a beam transport line supported by the isocentric rotary gantry 18.

The beam transport line comprises an inlet 24 for the hadron beam 17, an irradiation unit 100 for delivering a treatment beam 17' on a target volume 15 centered on the axis of rotation 22, as well as magnetic dipoles 19a, 19c for deflecting the beam and focusing means 20 for focusing the hadron beam, making it possible to transport the hadron beam 17 from the inlet 24 toward the irradiation unit 1. At the outlet of the irradiation unit 1, the treatment beam 17' is oriented substantially perpendicular to the axis of rotation 22. The irradiation unit 1 comprises a nozzle 2 generally comprising monitoring means in line with the beam, for example such as an ionization chamber. For treatments using passive delivery techniques for delivering the treatment beam, the nozzle 2 generally comprises customized accessories specific to each patient, such as a collimator and a compensator, to conform the dose deposition of the beam to the shape and size of the target volume 15, for example a tumor. For irradiation methods using dynamic delivery techniques for delivering the treatment beam, the nozzle 2 comprises scanning means 23 of the beam as well as monitoring means in line with the beam, for example such as an ionization chamber. Owing to the rotatability of the isocentric rotary gantry 18 about the axis of rotation 22, the irradiation unit 1 can rotate around the target volume 15, centered on the axis of rotation 22, to deliver the treatment beam 17' from different angles on said target volume 15.

Figure 2:
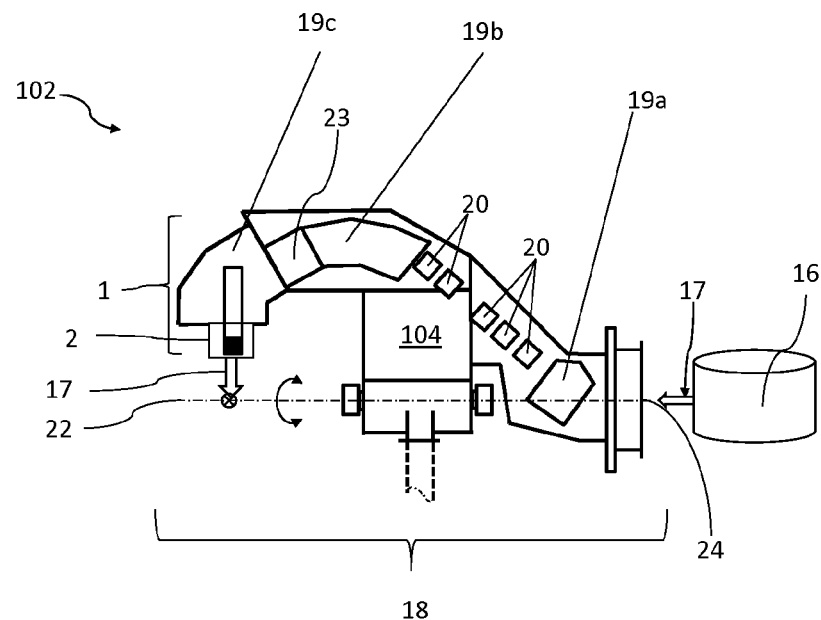
FIG. 2: is a very diagrammatic vertical cross-section of the hadron therapy installation according to a second embodiment.

FIG. 2 shows a second embodiment of the hadron therapy installation 102. This installation 102 differs from the installation 100 primarily in that it comprises a first 19a', second 19b' and third 19c' magnetic dipole, the third magnetic dipole 19c' having a bending angle smaller than 80°, which makes it possible to reduce the size of the rotary gantry. This embodiment is preferably intended for irradiation methods using dynamic delivery techniques for delivering the beam. In the second embodiment, the scanning means 23 are preferably situated between the second 19b' and third 19c' magnetic dipoles. In this embodiment, the irradiation unit comprises part of the third magnetic dipole 19c' and a nozzle 2 comprising monitoring means in line with the beam, for example such as an ionization chamber. Preferably, the beam transport line is supported by a pivoting arm 104, the angle of rotation of which about the axis of rotation 22 is generally limited to a value smaller than 360° (the angle of rotation is for example limited to 220°).

The present invention relates both to hadron therapy installations 100 of the traditional type, whereof the last magnetic dipole 19c has a bending angle greater than 80°, and new compact hadron therapy installations 102, whereof the last magnetic dipole 19c' has a bending angle smaller than 80°.

Figure 3:
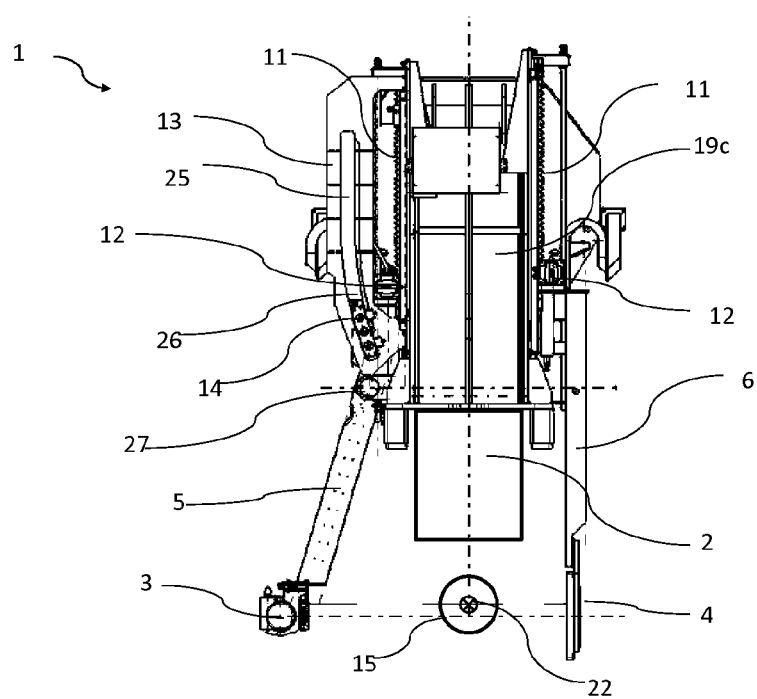
FIG. 3: is a cross-section perpendicular to the axis of rotation of an irradiation unit comprising an x-ray producing equipment and x-ray receiving equipment, which are shown in a deployed position.

FIG. 3 shows the irradiation unit 1 of the second embodiment in more detail using a cross-section perpendicular to the axis of rotation 22. One can in particular see the last magnetic dipole 19c' with the outlet nozzle 2.

Reference 3 indicates a piece of x-ray producing equipment, comprising an x-ray source. Reference 4 indicates a piece of x-ray receiving equipment. In FIG. 3, each of the two pieces of equipment 3 and 4 is shown in its deployed position, in which it is arranged in the immediate vicinity of the target volume 15. Situated on either side of the plane containing the axis of the treatment beam 17' and the axis of rotation 22, the two pieces of equipment 3 and 4 cooperate in this deployed position so as to form an XR imaging device.

The x-ray producing equipment 3 and the x-ray receiving equipment 4 are both secured in rotation with the irradiation unit 1 and translatable relative to the irradiation unit 1, between a retracted position, in which they are arranged at the irradiation unit 1, and the deployed position, in which they are arranged laterally relative to the target volume 15. The XR imaging device formed by the two deployed pieces of equipment 3 and 4, which are arranged on either side of the target volume 15, can rotate around said target volume 15 together with the irradiation unit 1.

In a preferred embodiment, as shown in FIG. 3, the x-ray producing equipment 3 is supported by a first arm 5 and the x-ray receiving equipment 4 is supported by a second arm 6.

Figures 4A, 4B:
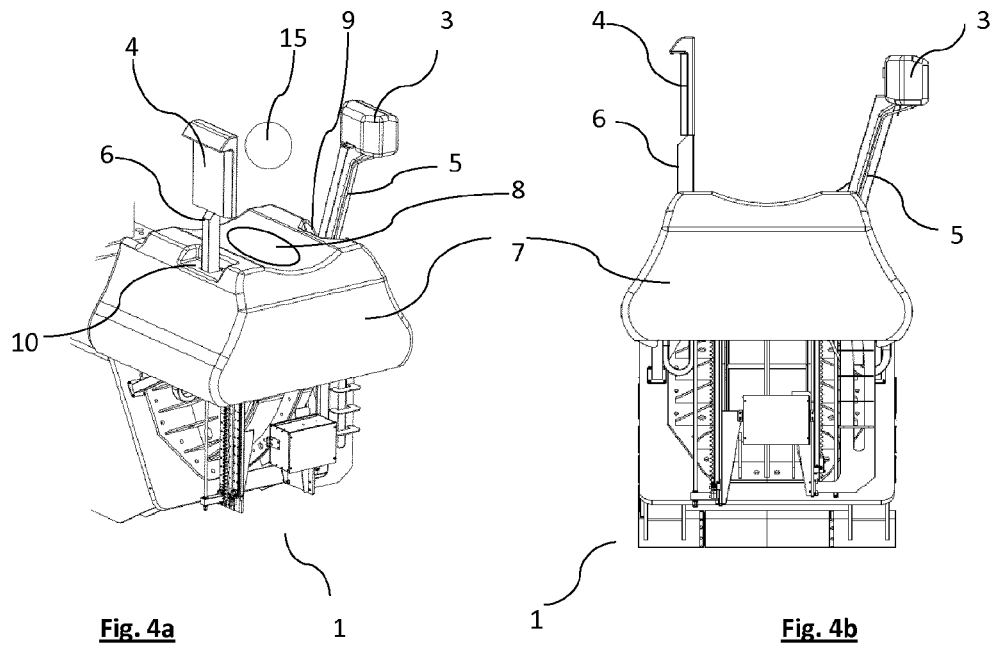
Figures 5A, 5B:
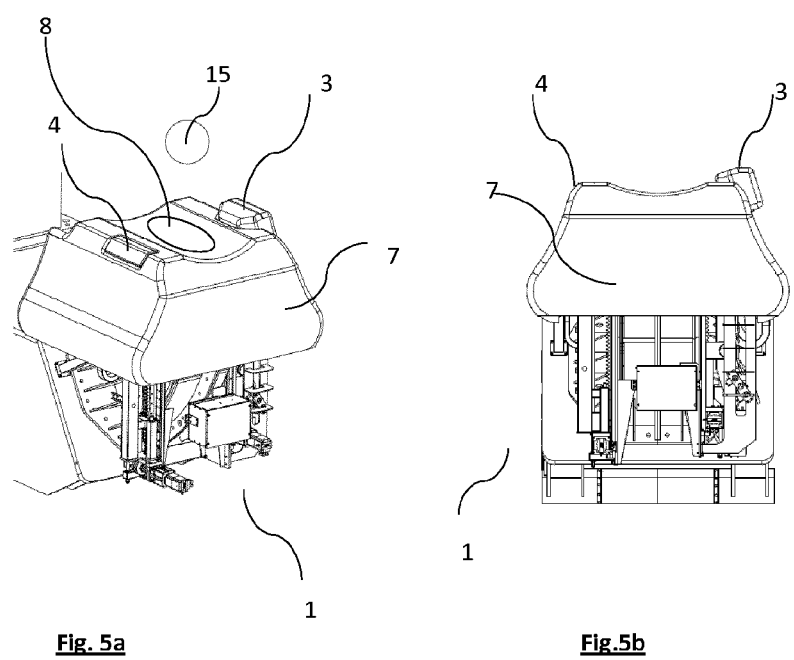

FIGS. 4a and 4b show two conceptual views of the irradiation unit 1 in a configuration where the x-ray producing equipment 3 and the x-ray receiving equipment 4 are arranged in the respective retracted positions. FIGS. 5a and 5b show two conceptual views of the irradiation unit 1 in a configuration where the x-ray producing equipment 3 and the x-ray receiving equipment 4 are arranged in their respective deployed positions.

Figure 6:
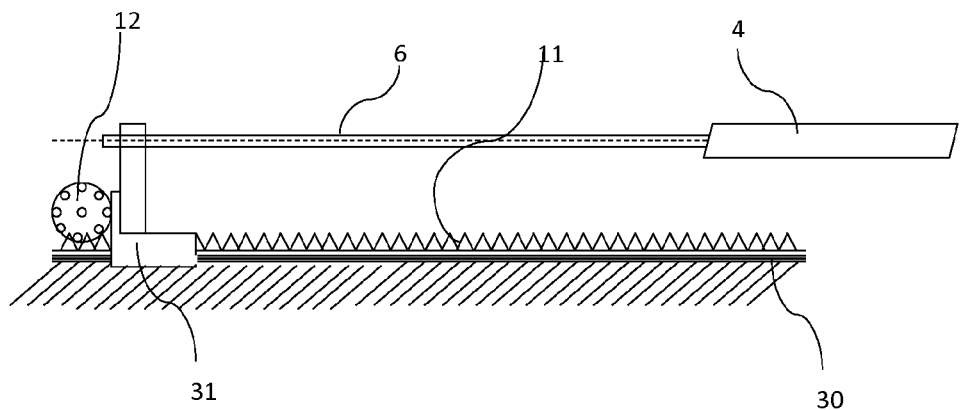
FIG. 6: is a diagram illustrating a device for guiding and driving the x-ray receiving equipment.
Figures 7A, 7B:
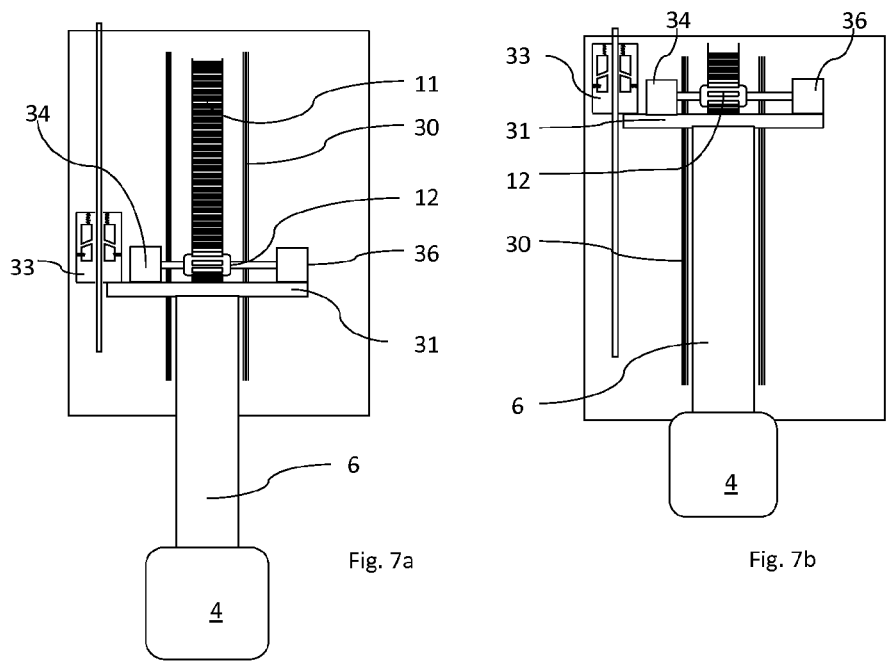
FIG. 7a: is a frontal view illustrating the device for guiding and driving the x-ray receiving equipment, the latter being shown in a deployed position.
FIG. 7b: is a frontal view like FIG. 7a, the x-ray receiving equipment being shown in a retracted position.

A preferred embodiment of a means for driving the x-ray receiving equipment 4 will be described hereafter using FIGS. 6, 7a and 7b.

In this preferred embodiment, the driving means comprises a rack 11 fastened on a side wall of the irradiation unit 1 or the casing of the deflecting magnet 19c, respectively, to another element rotating with the irradiation unit 1. This rack 11 is consequently immobile in a reference system secured to the irradiation unit 1. It extends in a direction substantially parallel to the direction of the treatment beam 17'.

At least one guide rail 30 forms a guide device for a cradle 31. This guide rail 30 is also fastened on the irradiation unit 1 or to another element rotating with the irradiation unit 1. It is further substantially parallel to the direction of the treatment beam 17'. FIGS. 7a and 7b show that the guide device of the cradle 31 comprises two parallel rails 30, which form a guide device that is immobile in a reference system secured to the irradiation unit 1.

A pinion 12, which is supported by the cradle 31 and rotated by a motor 36, meshes in the rack 11 to move the cradle 31 in its guide device 30 along the irradiation unit 1. The cradle 31 supports the arm 6 supporting the x-ray receiving equipment 4 rigidly. By rotating the motor 36 in one direction, the x-ray receiving equipment 4 supported by the second arm 6 is moved in rectilinear translation from its deployed position, shown in FIG. 7a, to its retracted position, shown in FIG. 7b. By rotating the motor 36 in the opposite direction, the x-ray receiving equipment 4 supported by the second arm 6 is moved in rectilinear translation from its retracted position, shown in FIG. 7b, to its deployed position, shown in FIG. 7a.

In one preferred embodiment, the means for driving the arm 6 further comprises a brake 33, for example an electric, hydraulic or pneumatic brake, combined with a detector system 34 for detecting the position of the cradle 31. This brake 33 makes it possible, together with the detection system 34 for detecting the position of the cradle 31, to immobilize the cradle 31 in any position of the rack 11, the power supply of the motor 36 then being cut.

One preferred embodiment of a means for driving the x-ray producing equipment 3 will be described hereafter using FIGS. 8a, 8b, 9a and 9b.

This preferred driving means of the x-ray producing equipment 3 comprises, like the preferred means for driving the x-ray receiving equipment 4 described above, a rack 11', a cradle 31', a guide device 30', a pinion 12' with a motor 36', as well as a brake 33' with a system 34' for detecting the position of the cradle 31'.

If the cradle 31 supports the second arm 6 supporting the x-ray receiving equipment 4 rigidly, the first arm 5 supporting the x-ray producing equipment 3 is connected to a support 29 of the cradle 31' using a cylindrical articulation 32. A pivoting device then makes it possible to pivot the first arm 5 about said cylindrical articulation 32, so as to cause the x-ray producing equipment 3 to move laterally away from the target volume 15, when the x-ray producing equipment comes closer to the target volume 15.

Figure 8A:
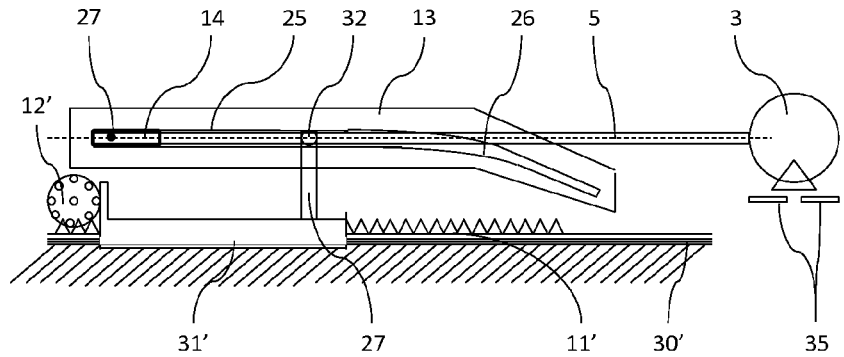
FIG. 8a: is a diagram illustrating a device for guiding and driving the x-ray producing equipment, the latter being shown in a retracted position.
Figure 8B:
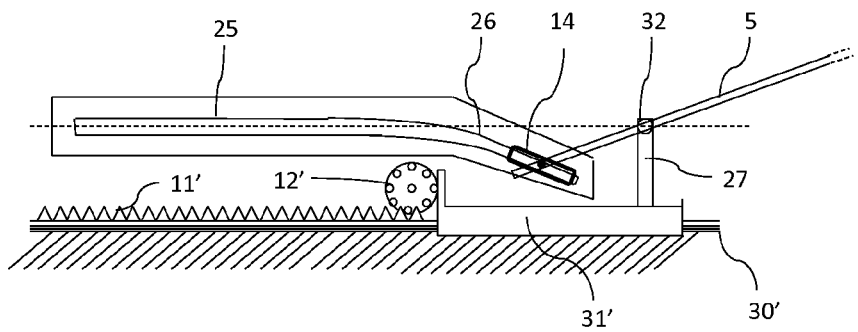
FIG. 8b: is a diagram illustrating a device for guiding and driving the x-ray producing equipment, the latter being shown in a deployed position.
Figure 9A:
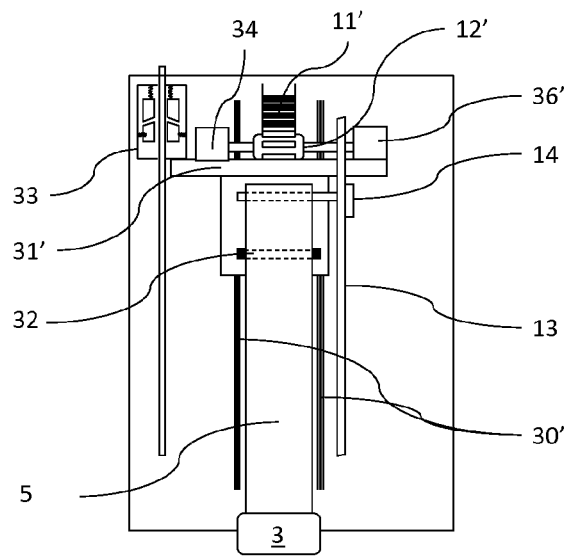
FIG. 9a: is a frontal view illustrating the device for guiding and driving the x-ray producing equipment, the latter being shown in a storage position.
Figure 9B:
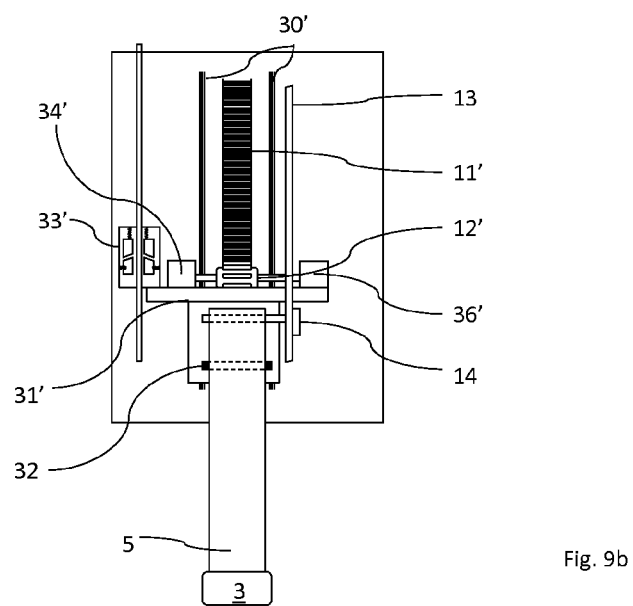
FIG. 9b: is a frontal view illustrating the device for guiding and driving the x-ray producing equipment, the latter being shown in the deployed position.

One preferred embodiment of this pivoting device is described using FIGS. 8a and 8b. The cylindrical articulation 32 is arranged between one end of the first arm 5 supporting the x-ray producing equipment 3 and an opposite end of the first arm 5. Said opposite end of the first arm 5 is connected via an articulation 27 to a slide 14, which is slidingly arranged in a guideway 13.

The guideway 13 is fastened on the irradiation unit 1 or on the casing of the last magnetic dipole 19c; in other words, it is immobile in a reference secured to the irradiation unit 1. It comprises a first linear guide portion 25, to guide the first arm 5 in a first translational movement starting from its retracted position, during which translational movement the first arm 5 remains substantially parallel to itself. A second curved guide portion 26 generates a pivoting movement of the first arm 5 about the cylindrical articulation 32. This pivoting movement is superimposed on the translational movement of the first arm, so as to cause the x-ray producing equipment 3 to move laterally away from the target volume 15, when the x-ray producing equipment 3 comes closer to the target volume 15. It will be noted that the slide 14 intersects the axis of rotation of the cylindrical articulation 32 and that the curved trajectory has a radius of curvature that brings the slide 14 closer to the irradiation unit 1, thereby separating the x-ray producing equipment 3 laterally relative to the target volume 15.

During the deployment of the x-ray producing equipment from its retracted position to its deployed position, the slide 14 first slides in the first linear guide portion 25 of the guideway 13, and the first arm 5 performs a translational movement, during which it remains parallel to itself. When the slide 14 enters the curved portion 26 of the guideway 13, the slide 14 imposes a lever movement on the arm 5 and causes the latter to pivot about the cylindrical articulation 32, which gives the first arm 5 a pivoting movement, which is superimposed on the translational movement. This pivoting movement causes the x-ray producing equipment 3 to move latterally away from the x-ray receiving equipment 4, so as to obtain an optimal source-detector distance, allowing both an optimal image resolution and rotation around the patient without risk of collision with the patient or the bed supporting the patient.

Figure 10:
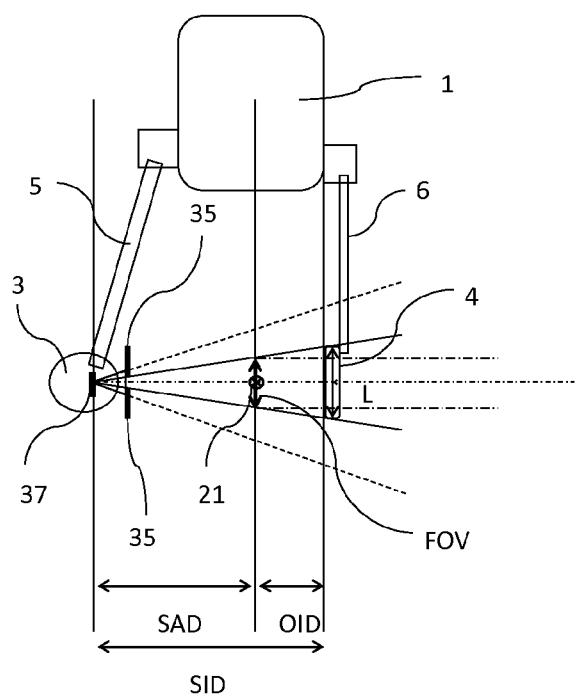
FIG. 10: is a diagrammatic view of one embodiment of the imaging device in which the geometric center of the x-ray receiving equipment is centered relative to an axis passing through an isocenter and through an x-ray producing source of a piece of x-ray producing equipment, so as to obtain a field of view FOV smaller than or equal to the surface of the x-ray receiving equipment.

Preferably, the SAD (Source-Axis Distance) indicated in FIG. 10, i.e., the distance between the x-ray source 37 of the x-ray producing equipment 3, when the latter is in its deployed position, and the axis of the treatment beam, is smaller than 1250 mm. Preferably, this SAD distance is comprised between 900 mm and 1100 mm, so as to avoid any risk of collision with the floor of the treatment area.

The x-ray receiving equipment advantageously comprises a detection panel with a length L comprised between 35 cm and 45 cm, for example L=40 cm, and with a width comprised between 20 cm and 40 cm. The enlargement factor of the object to be viewed is given by the relationship MR=SID/SAD, where MR is the enlargement factor, SID is the distance between the x-ray source 37 and the first detection panel 4, and SAD is the distance between the x-ray source 37 and the axis of the treatment beam. Advantageously, the enlargement factor MR is comprised between 1.5 and 2, more preferably it is comprised between 1.5 and 1.7, still more preferably it is comprised between 1.5 and 1.6. The field of view FOV, i.e., the anatomical region of the patient captured by the x-ray beam, is given by the relationship FOV=L/MR, where L is the length of the detection panel. Preferably, the detection panel is sized so as to be able to view a field of view FOV greater than or equal to 20 cm.

In one preferred embodiment of the invention, as shown in FIG. 9, the SID distance is approximately 1500 mm, the SAD distance is approximately 1000 mm, and the length of the panel is 40 cm. In this embodiment, the enlargement factor MR is therefore 1.5 and the maximum viewable field of view FOV is 26.67 cm.

Preferably, the detection panel 4 can be moved between several operational positions and the x-ray producing equipment then comprises collimators 35 that can be adjusted based on the operational position of the detection panel 4, so that the x-ray beam field coincides with the surface of the detection panel 4. It is thus possible to enlarge the field of view FOV by merging a first image obtained by the XR imaging device, when the detection panel 4 is in a first operational position, with a second image obtained by the XR imaging device, when the detection panel 4 is in a second operational position.

When the x-ray producing equipment 3 and the x-ray receiving equipment 4 are in their respective deployed positions, it is possible to carry out a cone beam computed tomography (CBCT) method by acquiring a series of images while rotating the rotary gantry around the patient. A computer device next makes it possible to process these images to reconstruct a three-dimensional image of the inside of a patient's body.

The described XR imaging device may also be used in the context of a fluoroscopic imaging method.

FIG. 4a shows that the irradiation unit 1 is covered by a cover 7 comprising: a first opening 8 for the passage of a treatment beam 17; a second opening 9 for the passage of the second arm 5, on which the x-ray producing equipment 3 is fastened; and a third opening 10 for the passage of the second arm 6, on which the x-ray receiving equipment 4 is fastened. The cover 7 in particular makes it possible to conceal and protect the mechanical parts of the driving means for the x-ray producing and receiving devices from the outside environment.

Preferably, the cover 7, with its openings 8, 9, 10, is sized so as to allow a complete or practically complete retraction of the x-ray producing equipment 3 and the x-ray detection device 4 inside the cover 7 (cf. FIGS. 5a and 5b).

Relative to the devices of the prior art, the imaging device takes up less space in the treatment area of the hadron therapy installation, whether in the position retracted inside the cover 7 or the deployed position outside the cover 7. Arranging the imaging device in its deployed position may additionally preserve easy access to the patient.

The arrangement of the x-ray producing 3 and x-ray receiving 4 devices has the advantage of avoiding collisions with the irradiation unit 1 or with other imaging devices during acquisition of images during a CBCT imaging session.

In one preferred embodiment, the hadron therapy installation comprises a movable floor that can be driven by the irradiation unit, for example such as a movable floor as described in documents WO2010076270 or in the Belgian or US patent applications filed that same day by the applicant, both incorporated by reference. In such installations, the irradiation unit 1 is advantageously surrounded by traction means of the moving floor.

Preferably, the traction means of the moving floor comprises a frame surrounding the irradiation unit 1 and connected to the irradiation unit by at least two fusible pistons. The frame also surrounds the means for driving the x-ray producing 3 and x-ray receiving 4 devices. More preferably, the traction device of the moving floor is surrounded by the cover 7 covering the irradiation unit 1. The cover 7 then further comprises openings to allow the connection between the moving floor and the traction means.

A cone beam computed tomography imaging method using a hadron therapy installation as described above comprises the following steps:
i) positioning a patient in a treatment area of the hadron therapy installation;
ii) deploying the x-ray producing 3 and x-ray receiving 4 equipment from their retracted positions to their deployed positions, in which the x-ray producing equipment 3 and the x-ray receiving equipment 4 are arranged on either side of a target volume 15 of the patient;
iii) acquiring a series of images using x-ray producing and receiving devices during rotation of the irradiation unit 1 around the target volume 15;
iv) computer processing of the obtained images to obtain a three-dimensional reconstruction of the inside of the patient's body.

According to one preferred embodiment of the method described above, the field of view FOV of the area to be imaged is first defined, and based on the source-detector SID and source-axis of the treatment beam SAD distances, the cone angle of the XR beam is calculated, as well as the surface necessary for the detection of the XR cone beam. Based on the size of the field of view to be imaged FOV, two cases may arise:
1) the field of view FOV is smaller than or equal to the ratio of the length of the detection panel to the enlargement factor L/MR, as shown in FIG. 9; or
2) the field of view FOV is larger than the ratio of the length of the detection panel to the enlargement factor L/MR, as shown in FIGS. 10a and 10b.

In the first case, after having positioned patient according to the aforementioned step i), the aforementioned step ii) is carried out, by aligning the center of the detection panel with the isocenter 21 and the x-ray source 37, and positioning the collimators 35 of the x-ray producing equipment 3 so as to project an x-ray beam cone covering the surface of the detection panel 4. The aforementioned steps iii) and iv) are then carried out.

Figures 11A, 11B:
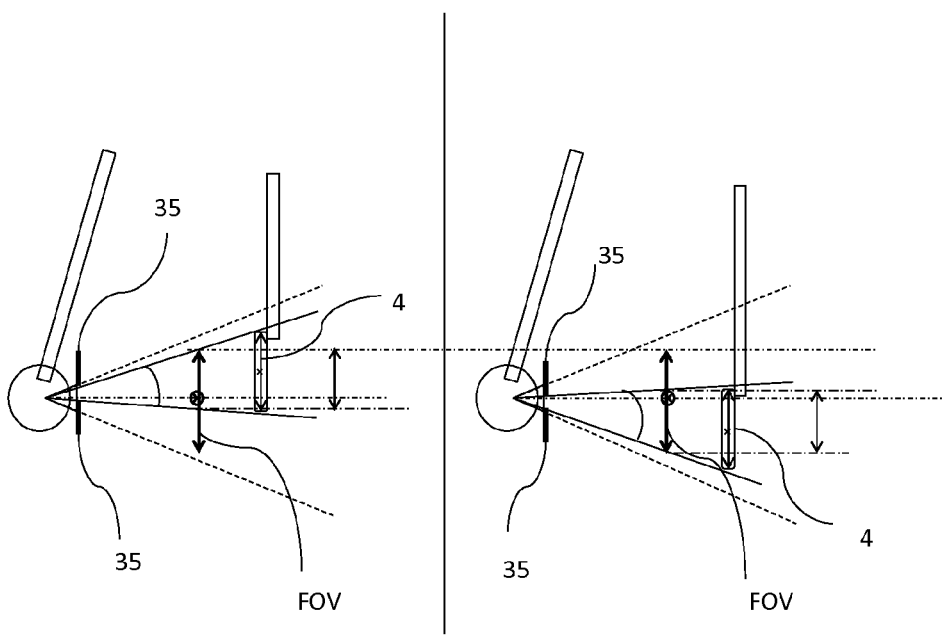
FIG. 11a, 11b: are two diagrammatic views of an embodiment of the imaging device making it possible to view a field of view FOV with a width larger than the ratio of the length of a piece of x-ray receiving equipment to an enlargement factor MR.

In the second case, after having positioned patient according to the aforementioned step i), the aforementioned step ii) is carried out, by positioning the detection panel so as to pick up a first portion of the cone of the x-ray beam, and positioning the collimators 35 so as to cover only the surface of the detection panel 4, as for example shown in FIG. 11a. The aforementioned step iii) is then carried out. The aforementioned step ii) is then carried out again, by repositioning the detection panel 4 so as to pick up a second portion of the cone of the x-ray beam having a slight overlap with the first portion, and positioning the collimators 35 so as to cover only the surface of the detection panel 4, as shown for example in FIG. 11b. The aforementioned steps iii) and iv) are then carried out.

A fluoroscopic imaging method using the x-ray producing equipment and the x-ray receiving equipment integrated into an irradiation unit 1 of the hadron therapy installation as described above comprises the following steps:
a) positioning a patient in a treatment area of the hadron therapy installation;
b) deploying the x-ray producing equipment 3 and the x-ray receiving equipment 4 from their first retracted position to their second deployed position;
c) viewing the movement of the patient's organs using x-ray producing and receiving devices, the rotation of the irradiation unit 1 being immobilized.

| List of references: | |
|---|---|
| 01 | irradiation unit |
| 02 | outlet nozzle of 01 |
| 03 | X-ray producing equipment |
| 04 | X-ray receiving equipment |
| 05 | first arm |
| 06 | second arm |
| 07 | cover 7 |
| 08 | first opening for passage of the treatment beam 17 |
| 09 | second opening for passage of the first arm 5 |
| 10 | third opening for passage of the second arm 6 |
| 11, 11' | rack |
| 12, 12' | pignon |
| 13 | guideway |
| 14 | slide |
| 15 | target volume |
| 16 | generator |
| 17 | hadron beam |
| 17' | treatment beam |
| 18 | isocentric rotary gantry |
| 19 | magnetic dipole |
| 20 | focusing means |
| 21 | isocenter |
| 22 | axis of rotation |
| 23 | scanning magnets |
| 24 | inlet of the beam transport line |
| | linear guide portion of 13 |
| 26 | curved guide portion of 13 |

-continued

List of references:

| | |
|---|---|
| 27 | articulation |
| 30, 30' | guide rail |
| 31, 31' | cradle |
| 32 | cylindrical articulation |
| 33, 33' | Pneumatic brake |
| 34, 34' | system for detecting the position of 31 |
| 36, 36' | motor |
| 37 | X-ray source |
| 100 | hadron therapy installation |
| 102 | hadron therapy installation |
| 104 | pivoting arm |

The invention claimed is:

1. A hadron therapy installation, comprising:
a support structure configured to rotate about an axis of rotation,
an irradiation unit supported by the support structure, so as to be able to rotate around a target volume centered on the axis of rotation to deliver a treatment beam from different angles onto the target volume;
an imaging device configured to move between a retracted position and a deployed position;
wherein the imaging device comprises a first drive unit for a first piece of equipment of the imaging device, the first drive unit comprising:
a first arm supporting the first piece of equipment;
a first cradle supporting the first arm the first arm configured to connect to the first cradle by an articulation element; and
a guide device coupled to the irradiation unit, configured to move in rotation with the irradiation unit and to guide the first cradle in translation along the irradiation unit, in a direction essentially parallel to the direction of the treatment beam, and configured to move the first piece of equipment in a lateral direction from the retracted position, in which it is located toward the irradiation unit, into the deployed position, in which it is located toward the target volume; and
a pivoting device to pivot the first arm about the articulation element, so as to cause the first equipment to move laterally away from the target volume, when the first piece of imaging equipment moves from the retracted position to the deployed position.

2. The installation according to claim 1, wherein the imaging device comprises:
x-ray producing equipment; and
x-ray receiving equipment;
wherein, in the deployed position of said imaging device, the x-ray producing equipment and the x-ray receiving equipment are arranged on either side of the target volume, and wherein the x-ray producing equipment preferably forms the first piece of equipment.

3. The installation according to claim 2, wherein the imaging device further comprises a second drive unit for a second piece of equipment, the second drive unit comprising:
a second arm bearing the second piece of equipment of the imaging device;
a second cradle supporting the second arm; and
a second guide device arranged alongside the irradiation unit and configured to move in rotation with the irradiation unit, so as to be able to guide the second cradle along the irradiation unit to move the second piece of equipment supported by the second arm from the retracted position into the deployed position;
wherein the first arm and the second arm are arranged on either side of a plane containing the axis of rotation and the axis of the treatment beam.

4. The installation according to claim 3, wherein at least one of the first or second drive unit further comprises:
a pinion supported by at least one of the first or second cradle and rotated by a motor; and
a rack arranged such that the pinion is configured to mesh in the rack to move at least one of the first or second cradle in at least one of the first or second guide device along the irradiation unit.

5. The installation according to claim 4, wherein:
the pivoting device of the first arm comprises:
a guideway configured to be immobile relative to the irradiation unit, and
a slide connected to the first arm by the articulation element and configured to move in the guideway,
the guideway comprising:
a linear guide portion configured to impart a translational movement to the first arm starting from the retracted position; and
a curved guide portion configured to give the first arm a pivoting movement about the articulation element, wherein the pivoting movement is configured to be superimposed on the translational movement so as to cause the first piece of imaging equipment to move laterally away from the target volume during movement of the first piece of equipment from the retracted position to the deployed position.

6. The installation according to claim 5, wherein
the irradiation device comprises a cover forming an outer casing of the irradiation unit; and
the cover comprises, on the side facing the target volume:
a first opening configured to allow passage of the treatment beam;
a second opening configured to allow passage of the first arm; and
a third opening configured to allow passage of the second arm, wherein the second arm is configured to support a second piece of equipment of the imaging device.

7. The installation according to claim 6, wherein at least one of the first piece of equipment or the second piece of equipment is, in the retracted position, completely inside the cover.

8. The installation according to claim 2, wherein:
the x-ray producing equipment comprises an x-ray source and a collimator positioned between the x-ray source and the x-ray receiving equipment; and
the x-ray receiving equipment comprises an x-ray detection panel.

9. An imaging method in the hadron therapy installation according to claim 8, comprising:
deploying the imaging device from the retracted position to the deployed position; and
acquiring images while the irradiation unit pivots around the target volume.

10. The imaging method according to claim 9, further comprising:
performing cone beam computed tomography in a zone of the patient to be treated, wherein performing cone beam computed tomography comprises:

positioning the patient in the treatment area in the hadron therapy installation;

deploying the x-ray producing equipment and the x-ray receiving equipment from the retracted position toward the deployed position, in which the x-ray producing equipment and the x-ray receiving equipment are positioned on opposite sides of the target volume of the patient; and acquiring radiographic images during pivoting of the irradiation unit around the target volume.

11. The method according to claim 10, further comprising:

defining a field of view of a zone to be imaged;

calculating a cone angle of an x-ray beam and the surface area necessary for the detection of the x-ray beam, based on a source-detector distance and a source-treatment beam axis distance; and comparing a size of the field of view to be imaged to a ratio of a length of a detection panel to an enlargement factor wherein:

when the field of view is smaller than or equal to the ratio of the length of the detection panel to the enlargement factor:

performing cone beam computed tomography, and processing the obtained images to obtain a three-dimensional reconstruction of the target volume; and when the field of view is greater than the ratio of the length of the detection panel to the enlargement factor:

deploying the x-ray producing equipment and the x-ray receiving equipment from the retracted position toward the deployed position, in which the x-ray producing equipment and the x-ray receiving equipment are positioned on opposite sides of the target volume of the patient;

positioning the detection panel to capture a first portion of the x-ray beam cone, and positioning the collimators to cover only the surface of the detection panel;

acquiring radiographic images during pivoting of the irradiation unit around target volume;

deploying the x-ray producing equipment and the x-ray receiving equipment toward again, wherein the detection panel is repositioned to pick up a second portion of the x-ray beam cone overlapping the first portion, and the collimators are positioned to cover only the surface of the detection panel;

acquiring radiographic images during pivoting of the irradiation unit around target volume; and processing the obtained images to obtain a three-dimensional reconstruction of the target volume.

12. The method according to claim 11, further comprising:

performing fluoroscopy in an area of the patient to be treated, wherein performing fluoroscopy comprises:

positioning the patient in the treatment area of the hadron therapy installation;

deploying the x-ray producing equipment and x-ray receiving equipment from the retracted position toward the deployed position; and viewing the movement of the organs of the patient using the x-ray producing equipment and the x-ray receiving equipment, while the rotation of the irradiation unit is immobilized.

13. A hadron therapy system, comprising:

a support structure configured to rotate about an axis of rotation;

an irradiation device, supported by the support structure and configured to rotate around a target volume centered on the axis of rotation, to deliver a treatment beam from different angles onto the target volume;

an imaging device comprising a first imaging component and a drive unit configured to move the first imaging component in a lateral direction between a retracted position, at which the first imaging component is located toward the irradiation device, and a deployed position, at which the first imaging component is located toward the target volume;

wherein the drive unit further includes:

a first arm connected to the first imaging component at a distal end of the arm;

a cradle supporting the first arm and configured to move alongside the irradiation device, wherein the cradle is further configured to pivotably support the first arm between the distal end and a proximal end, and wherein the first arm is connected to the cradle by an articulable element;

a guide device arranged alongside the irradiation device and configured to: move in rotation with the irradiation device so as to guide the cradle alongside the irradiation device in a direction parallel to the direction of the treatment beam, and move the first imaging component from the retracted position to the deployed position, wherein:

the first imaging component is located toward the irradiation device in the retracted position, the first imaging component is located toward the target volume in the deployed position, and the guide device comprises a curved guide portion for generating a pivoting movement of the first arm; and a pivoting device to pivot the first arm about the articulable element and thereby cause the first imaging component to move laterally away from the target volume during movement of the first imaging component from the retracted position to the deployed position.

14. The system according to claim 13, wherein:

the first piece of the imaging device comprises x-ray producing equipment;

the imaging device further comprises x-ray receiving equipment; and when the imaging device is in the deployed position, the x-ray producing equipment and the x-ray receiving equipment are arranged on either side of the target volume.

15. The system according to claim 14, wherein:

the x-ray producing equipment comprises an x-ray source and a collimator positioned between the x-ray source and the x-ray receiving equipment; and the x-ray receiving equipment comprises an x-ray detection panel.

16. The system according to claim 13, wherein:

the irradiation device comprises a cover forming an outer casing of the irradiation device; and the cover comprises, on the side facing said target volume:

a first opening configured to allow passage of the treatment beam;

a second opening configured to allow passage of the first arm; and a third opening configured to allow passage of a second arm.

17. The system according to claim 16, wherein the x-ray producing equipment and the x-ray receiving equipment are, in the retracted position, at least partially contained by the cover.

* * * * *